United States Patent
Heidsieck

[11] Patent Number: 5,528,649
[45] Date of Patent: Jun. 18, 1996

[54] METHOD OF CALIBRATING A RADIOLOGICAL SYSTEM AND OF MEASURING THE EQUIVALENT THICKNESS OF AN OBJECT

[75] Inventor: Robert Heidsieck, Versailles, France

[73] Assignee: General Electric CGR SA, Issy les Molineaux, France

[21] Appl. No.: 979,471

[22] Filed: Nov. 20, 1992

Related U.S. Application Data

[63] Continuation of Ser. No. 829,574, Feb. 3, 1992, abandoned, which is a continuation of Ser. No. 535,520, Jun. 8, 1990, abandoned.

[30] Foreign Application Priority Data

Jun. 9, 1989 [FR] France .................................. 89 07686

[51] Int. Cl.$^6$ ............................................. G01N 23/06
[52] U.S. Cl. .................................... 378/56; 378/207
[58] Field of Search ............................ 378/207, 56

[56] References Cited

U.S. PATENT DOCUMENTS

| | | | |
|---|---|---|---|
| 2,258,593 | 10/1941 | Black | 378/207 |
| 2,399,650 | 5/1946 | Moyer | 378/207 |
| 3,334,231 | 8/1967 | Bernstein | 378/207 |
| 3,343,231 | 8/1967 | Bernstein | 378/207 |
| 4,763,343 | 8/1988 | Yanaki | 378/110 |

FOREIGN PATENT DOCUMENTS 2004437  3/1979  United Kingdom.

OTHER PUBLICATIONS

"Introduction to X-Ray Spectrometric Analysis", Bertin, Plenum Press, 1978, pp. 59, 60.
Geise, Richard et al, Medical Physics, "Routine quality control tests for film-screen mammographic systems with automatic exposure control", 1988, vol. 15, No. 6, pp. 904–908.
Pasini, Daniel et al, Applied Physics, "In-situ calibra-technique for x-ray films", 1984, vol. 23, No. 6, pp. 762–766.
Johns, H. E. et al, *The Physics of Radiology*, Fourth Ed., pp. 58, 59, 146 and 147.

*Primary Examiner*—Craig E. Church
*Attorney, Agent, or Firm*—Walter C. Farley

[57] ABSTRACT

The calibration method consists in measuring the efficiency D of a detector cell placed behind the object as a function of various phantom thicknesses $E_p$ and various X-ray tube supply voltages $V_m$. These measurements enable an analytic model $D=f(V_m, E_p)$ to be determined describing the resulting curves. The inverse function of this analytic model can be used for calculating thickness $E_p$ as a function of the measured efficiency D and the known supply voltage $V_m$.

35 Claims, 1 Drawing Sheet

METHOD OF CALIBRATING A RADIOLOGICAL SYSTEM AND OF MEASURING THE EQUIVALENT THICKNESS OF AN OBJECT

This application is a continuation of Ser. No. 07/829,574 filed Feb. 3, 1992, now abandoned which is a continuation of application Ser. No. 07/535,520 filed Jun. 8, 1990, now abandoned.

FIELD OF THE INVENTION

This invention relates to radiological systems for examining objects, and more particularly, in such systems, the invention relates to a method of calibrating a radiological system and of measuring the equivalent thickness of an object to be examined.

BACKGROUND OF THE INVENTION

A radiological system essentially comprises an X-ray tube and a detector of such rays with an object to be examined such as the portion of the body of the patient being interposed therebetween. The detector (which may be constituted by a film-screen pair, for example), provides an image of the object after being exposed for an appropriate length of time and after the film has been developed. The quality of the image depends both on the characteristics of the object and on the parameters of the radiological system.

The radiological properties of an object are given by its thickness and by its composition, and these properties vary firstly from one patient to another and secondly from one part of the body to another. It is difficult to determine these characteristics accurately: in particular, it is difficult or even impossible to determine the composition of an object merely by means of a physical examination. The notion of equivalent thickness, as known in radiology, serves to reduce knowledge about these two variables to a problem in one dimension.

The equivalent thickness of an object is defined relative to a reference substance such as plexiglass or a substance simulating the absorption of an organ of given composition. Under accurate radiological conditions, i.e. with fixed configuration and exposure parameters, the equivalent thickness of an object placed in the radiation field is represented by the thickness of the reference substance that would provide the same quantity of energy at the detector, i.e. the same optical density when the detector is a film.

A doctor can make use of knowledge about the equivalent thickness of an object, for example, as a medical indication or for establishing statistics about patients.

The equivalent thickness of an object also depends on parameters of the radiological system. These parameters are generally classified in two categories:

"radiological" parameters such as the voltage V of the X-ray tube, the current I taken by the tube, the exposure time S, and the product I×S which defines the quantity of energy emitted; and "configuration" parameters which are all of the parameters other than the radiological parameters that have an effect on the quality of the incident radiation on the detector, and not including the object.

For example, these configuration parameters may be:

a) the selected track of the rotary anode in the X-ray tube;

b) the selected size of the focus in the X-ray tube;

c) the selected filter interposed on the path of the beam of X-rays;

d) the selected magnification;

e) the selected distance between the focus and the image receiver;

f) the selected image receiver; and g) the selected types of accessory present in the beam of X-rays, e.g. a compression pad, an anti-diffusion screen, etc.

SUMMARY OF THE INVENTION

An object of the present invention is to implement a method of calibrating a radiological system making it possible to determine the relationships between the radiological parameters of the system, the object to be X-rayed, and a magnitude characteristic of the radiation spectrum that has passed through the object.

Another object of the invention is to implement a method of measuring the equivalent thickness of an object.

The invention provides a method of calibrating a radiological system designed to examine an object, the system comprising: an X-ray tube whose supply voltage V can take up various different values $V_m$, varying either continuously or discretely, the tube emitting a beam of X-rays in the form of bursts of variable duration S; and a detector cell for detecting X-rays that have passed through the object to be examined and serving to convert a physical magnitude characteristic of the beam of X-rays into a measurement signal M such as an electrical signal; the method being characterized in that it comprises the following operations:

(a) selecting a physical magnitude A characteristic of the object to be observed;

(b) choosing a class of reference objects comprising n objects or phantoms for which the physical magnitude takes up n known values;

(c) selecting j values $V_m$ of the supply voltage for the X-ray tube at which calibration is to be performed;

(d) selecting the value of the product I×S of the anode current taken by the X-ray tube during the exposure time S for each phantom associated with each value of the supply voltage $V_m$;

(e) installing a phantom on the path of the X-rays, adjusting the supply voltage to a value $V_m$, and integrating the radiation that passes through the phantom as detected by the detector cell between the beginning of measurement and the instant at which the product I×S is equal to the value selected in operation (d), thereby obtaining a measurement M;

(f) calculating the efficiency D as given by the ratio M/I×S;

(g) reiterating operations (e) and (f) for the same phantom but for the (j−1) other values of the supply voltage $V_m$;

(h) reiterating operations (e), (f), and (g) for the (n−1) other phantoms;

(i) using a conventional estimation method to determine the analytic model $D=f(V_m,A)$ relating the values of efficiency D to the values of the physical magnitude A and of the voltage $V_m$; and (j) determining the inverse function of $f(V_m,A)$, written $g(V_m,D)$ enabling A to be determined given $V_m$ and D.

The operations (d) and (e) may be replaced by the following operations:

(d') selecting the exposure time S for each phantom associated with each value of the voltage $V_m$; and (e') placing a phantom on the path of the X-ray, adjusting the supply voltage to a value $V_m$, measuring the product I×S of the anode current taken by the X-ray tube for the exposure time S, and integrating the radiation that passes through the phantom as detected by the detector cell during the exposure time S as selected during operation (d'), thereby obtaining a measurement M.

When the radiological system has several possible configuration parameters, the method includes an additional operation consisting in:

(k) reiterating operations (e) or (e') to (j) for each value of the configuration parameters.

When the configuration parameters can be grouped into classes, the various operations (e) or (e') to (j) are performed for a reference configuration of each class (C), and for each element of the class (C) a weighting coefficient is determined relative to the reference configuration by measuring the efficiency D at a voltage $V_m$ and for a given value of the physical magnitude A, and by defining the weighting coefficient of the configuration as the ratio between said measured efficiency D and the efficiency measured under analogous conditions using the reference configuration. In order to improve the accuracy of this coefficient, the value used may be the result of averaging efficiency ratios as defined above and as measured under various radiological conditions.

In numerous radiological systems, the physical magnitude A will be the thickness of the phantom along the path of the X-rays. The calibration method of the invention can thus be used to determine the thickness $E_p$ of a phantom if $V_m$ and D are known. Thus, if the same values of $V_m$ and D are obtained for an object put in the place of the phantom, it will be deduced that the equivalent thickness of the object relative to the phantom is $E_p$. Use can be made of this value by communicating it to the operator via an appropriate display device or by recording it for subsequent use. The above-described calibration method can thus be used for measuring the equivalent thickness of an object by means of a radiological system.

BRIEF DESCRIPTION OF THE DRAWING

Other features and advantages of the present invention will appear from reading the following description of the invention made with reference to the accompanying drawings, in which.

DESCRIPTION OF THE PREFERRED EMBODIMENTS

Figure 1:
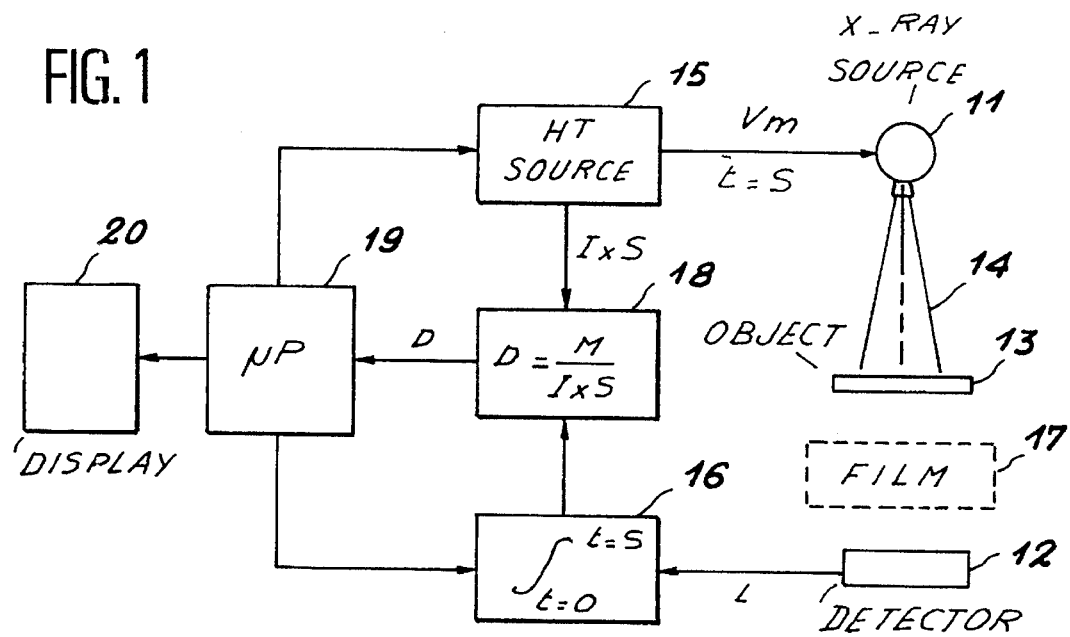
FIG. 1 is a block diagram of a radiological system that can be used for implementing the calibration method of the invention.

A radiological system to which the calibration method of the invention applies comprises at least one X-ray source 11 and an X-ray detector cell 12 disposed downstream from an object 13 in the propagation direction of the X-rays, as represented in FIG. 1 by a beam 14 of X-rays.

The source 11 is associated with a power supply 15 which provides a variable high supply voltage $V_m$ for a variable length of time S referred to as the exposure time. During an exposure, the X-ray tube of the source 11 has an anode current I flowing therethrough. The detector cell 12 serves to convert a physical magnitude characteristic of the X-ray beam 14 such as its kerma or its energy fluence, into a measurement signal L, e.g. an electrical signal. The electrical signal L provided by the detector cell 12 is applied to a circuit 16 which integrates the electrical signal throughout the exposure time S. The result of the integration is a signal M which is a measurement of the radiation that has passed through the object 13 during the exposure time.

The radiological system outlined briefly above does not make an image of the object. In order to make an image, a receiver 17 such as a sensitive film should be added, with the film being placed between the object 13 and the detector cell 12, or else downstream therefrom. In a third embodiment of the radiological system, the detector cell 12 may be incorporated in the receiver 17. The calibration method consists firstly in selecting a class of reference objects or phantoms and in performing radiation measurements, also called operating measurements, for each phantom and for various different values $V_m$ of the voltage supplied to the X-ray source 11. Within the class of reference objects, the variable may be, for example, the thickness $E_p$ of the phantom extending perpendicularly to the X radiation. This thickness $E_p$ constitutes the physical magnitude A which characterizes the object to be observed. The radiation measurement used is efficiency D which is defined as being the ratio between the value M provided by the circuit 16 and the product I×S. By choosing such a ratio to define the efficiency D, efficiency is independent of exposure time S and of various different values of tube current.

The efficiency D is calculated by means 18 which receive the signal M from the circuit 16 and which also receive information concerning the product I×S from the power supply 15.

Of course, if the current I is not constant throughout the exposure time, then the product I×S should be replaced by the integral of the anode current taken over the exposure time.

Similarly, the efficiency D could be measured over a fraction of the exposure time providing the signal M is obtained by integrating the signal L over the same integration period as is used for the anode current I.

Thus, once the set of phantoms has been determined, the calibration method consists in measuring the efficiency for each phantom at specified supply voltages $V_m$.

More precisely, using a first phantom of thickness $E_1$, the efficiency $D_{1m}$ is measured for each value $V_m$ of the supply voltage, with the different values $V_m$ constituting a determined set. These values of $D_{1m}$ as a function of voltage $V_m$ may be plotted on a graph in order to obtain points 21' in FIG. 2.

Figure 2:
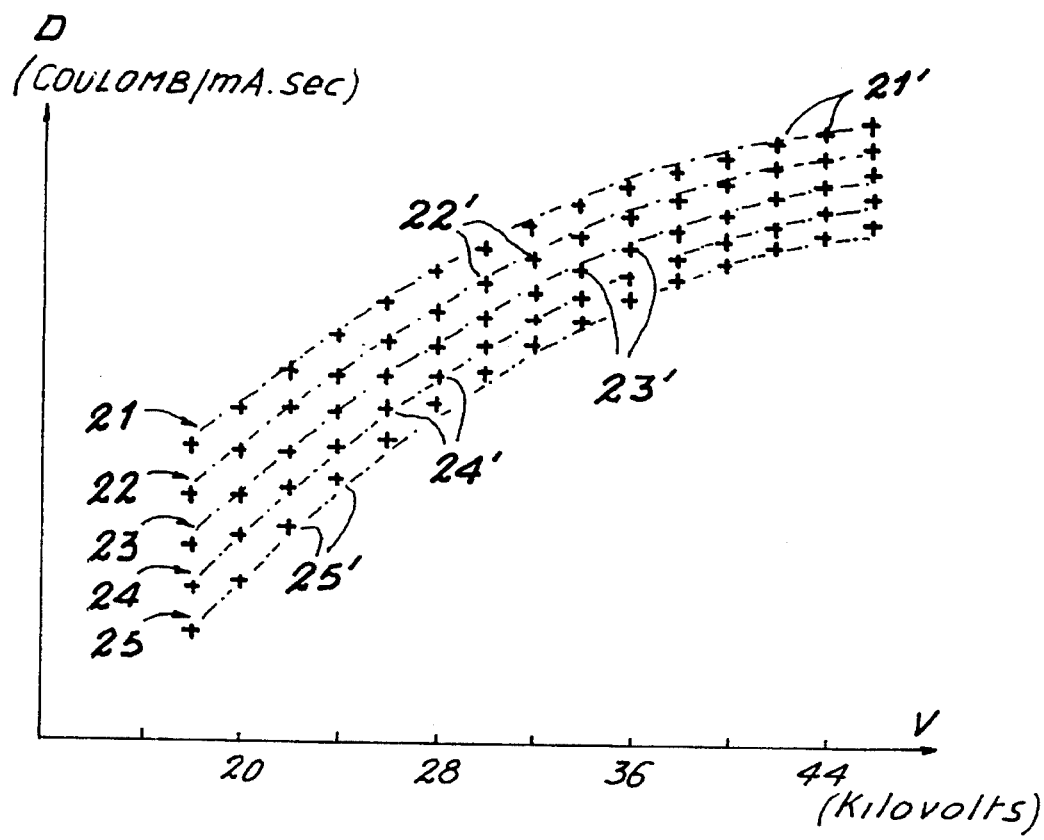
FIG. 2 is a graph showing curves obtained by implementing the calibration method of the invention.

The efficiency D is measured using a different phantom of thickness $E_2$, thereby obtaining values $D_{2m}$ corresponding to points 22' in FIG. 2, and so on, thereby obtaining other series of points 23, 24, and 25' corresponding respectively to efficiencies $D_{3m}$, $D_{4m}$, and $D_{5m}$, and to thicknesses $E_3$, $E_4$, and $E_5$.

It should be observed that in FIG. 2, the efficiencies $D_{pm}$ are plotted up the Y axis using a logarithmic scale whereas the supply voltages are plotted along the X axis using a linear scale from 20 kilovolts to 44 kilovolts. These series of points 21' to 25' are used to define the parameters of an analytic model which describes the behavior of the efficiency D as a function of the parameters $V_m$ and $E_p$ for a given configuration of the radiological system. This analytic model is written:

$$D = f(V_m, E_p) \tag{1}$$

The parameters of the analytic model may be adjusted using conventional estimation tools such as the least squares method.

The curves 21 to 25 represent the values of the efficiency D given by the analytic model represented by the equation:

$$D = f(V_m, E_p) = \exp[f_1(V_m) + E_p \times f_2(V_m)] \quad (2)$$

in which $f_1(V_m)$ and $f_2(V_m)$ are second degree polynomials which can be written as follows:

$$f_1(V_m) = A_0 + A_1 V_m + A_2 V_m^2$$

$$f_2(V_m) = B_0 + B_1 V_m + B_2 V_m^2$$

The inverse of the function expressed by equation (2) can be used for calculating $E_p$ if D and $V_m$ are known, by using the following equation (3):

$$E_p = g(V_m, D) = \frac{Ln(D) - f_1(V_m)}{f_2(V_m)} \quad (3)$$

given that $f_2(V_m)$ cannot be zero for common values of $V_m$ since the efficiency D always depends on the thickness $E_p$ at the voltage $V_m$ under consideration.

In other words, for each pair of values $(E_p, V_m)$ there is a corresponding efficiency measurement D, thereby enabling $E_p$ to be determined as a function of $V_m$ and D. During radiological examination, a measured efficiency D performed with a given supply voltage $V_m$ can be used to determine an equivalent thickness expressed in the units used for $E_p$.

A preferred application consists in mammographic examinations, given the small variation in the composition of mammary tissue.

To sum up, the method of calibrating a radiologic system consists in performing the following operations:

(a) selecting a physical magnitude A which characterizes the object to be observed, e.g. the thickness $E_p$ of the object;

(b) selecting n reference objects or phantoms for which the magnitude A (thickness $E_p$) differs from one phantom to the next;

(c) selecting j values $V_m$ of the supply voltage (circuit 15) applied to the X-ray tube for calibration purposes;

(d) selecting the value of the product I×S of the current I taken by the X-ray tube during the exposure time S for each phantom associated with each voltage value $V_m$;

(e) installing a phantom, adjusting the voltage to a value $V_m$, and measuring M (circuit 16) when the product I×S is equal to the value selected during operation (d); and (f) calculating the efficiency D=M/I×S in the means 18, thereby giving one of the points on one of the curves in FIG. 2.

The efficiency D is calculated for each of the j values of the supply voltage $V_m$ without moving the phantom, i.e., by:

(g) reiterating operations (e) and (f) for the same phantom but using (j−1) other values of the supply voltage $V_m$.

A set of points is thus obtained, such as that represented by the points 21' in FIG. 2, for example. In order to obtain a complete array of points (22' to 25') as shown in FIG. 2, it is necessary to:

(h) reiterate operations (e), (f), and (g) for the (n−1) other phantoms.

In practice, the n values of A (thickness $E_p$), the j values of the supply voltage $V_m$, and the (n×j) values of D are delivered to a microprocessor 19 which, by means of suitable software, performs the following operation:

(i) using a conventional estimation method to determine the analytic model D=f($V_m$, A) relating the values of the efficiency D to the values of the physical magnitude A (thickness $E_p$) and of the voltage $V_m$.

Finally, the microprocessor 19 calculates the inverse function of f($V_m$,A) that enables A (thickness $E_p$) to be determined as a function of $V_m$ and D. This function is written g($V_m$, D).

In a variant of the calibration method, the operation (d) may be replaced by an operation (d') which consists in selecting an exposure time S for each phantom associated with each value of the voltage $V_m$. In this case, the operation (e) is modified to measure M and the product I×S during the exposure time S selected during operation (d').

In the calibration method described above, it has been assumed that only the thickness of the phantom and the radiological parameters of the system are changed, with the other or "configuration" parameters such as a filter remaining identical. It will therefore be understood that the calibration method must be repeated after changing a single configuration parameter, e.g. the filter. This may give rise to a different analytic model providing a different formulation for thickness $E_p$ as a function of D and $V_m$.

Since there are numerous configuration parameters that may have an effect, such a procedure gives rise to numerous manipulations. The number of such calibration manipulations can be reduced by observing that some of these parameters are interdependent. These configurations constitute classes C having the following property: the efficiencies D which are measured for each of the configurations defined by a class C can be deduced from one another by a weighting coefficient for analogous radiological conditions. This weighting factor is due to the fact that the incident energy spectra on the detector are similar or very close in each of the classes.

In order to reduce the number of calibration operations, the invention proposes selecting, for each class (C), a reference configuration and performing a full calibration operation thereon as described above. Thereafter, a weighting factor needs to be determined for each element in the class (C) compared with the reference configuration by measuring the efficiency D at a supply voltage $V_m$ for a given value of the physical magnitude A, and by defining the weighting factor of the configuration as being equal to the ratio between this measurement of the efficiency D and the efficiency measured under analogous conditions using the reference configuration. In order to improve the accuracy of this coefficient, the value used may be the result of taking the mean of efficiency ratios as defined above and as measured under various radiological conditions. This mean may be calculated using efficiency ratios measured on several times over for the same element in the class (C) under the same radiological conditions. It may alternatively be calculated using efficiency ratios measured on one or more occasions with various different phantoms and for various values of the supply voltage $V_m$.

Further, if the function f($V_m$, A) is assumed to be separable into two functions, it is possible to reduce the number of calibration measurements by measuring the efficiency D for various values $V_m$ of the supply voltage, while $E_p$ is fixed, and then by measuring efficiency D for different values of thickness $E_p$ while $V_m$ is fixed. In the first case, the following function is obtained:

$$G_{E_p}(V_m) = f(V_m, E_p) \text{ for fixed } E_p$$

and in the second case the following function is obtained:

$$H_{V_m}(E_p) = f(V_m, E_p) \text{ for fixed } V_m.$$

Thus, when the function f($V_m$, $E_p$) is separable into two functions, then:

$$f(V_m, E_p) = G_{E_p}(V_m) \times H_{V_m}(E_p)$$

The functions $G_{E_p}(V_m)$ and $H_{V_m}(E_p)$ may be defined analytically as follows. Firstly, for each of these functions, the degree of the polynomial suitable for describing its curve is determined, after which the coefficients of the polynomial are determined using an estimation method. In order to implement this method, it is necessary to make (n+j) measurements whereas (n×j) measurements are required using the method of FIG. 2. The invention is described above using phantoms of determined thickness $E_p$, however it is clear that the phantoms could be arbitrary and, in particular, they need not be rectangular in shape, for example they could be cylindrical.

Once a radiological system has been calibrated in the manner described above, it is operational for measuring the equivalent thickness of an object. This measurement takes place using the following steps:

(1) placing the object on the path of the radiation;

(2) adjusting the tube supply voltage $V_m$ by means of the power supply 15;

(3) measuring the efficiency D using the means 18 which receive information concerning the values $V_m$, I, and S, from the power supply 15, and information concerning the measured radiation M from the circuit 16;

(4) using the microprocessor 19 to calculate the equivalent thickness $E_p$ using the formula $E_p = g(V_m, D)$; and (5) displaying the result of the calculation on a display device 20.

The display device 20 may be replaced by any other means for making use of the thickness $E_p$, e.g. a computer file, a printer, or a calculator.

What is claimed is:

1. A method of calibrating a radiological system for examining an object (13) wherein the system is of the type including an X-ray tube (11) having a supply voltage V adjustable to various different values $V_m$ either continuously or discretely, the tube emitting a beam of X-rays in the form of bursts of variable duration S, and having an anode current I, and a detector cell for detecting X-rays that have passed through the object to be examined and for converting a physical magnitude characteristic of the beam of X-rays into a measurement signal M such as an electrical signal, the method comprising the steps of:

(a) selecting a physical magnitude A which is characteristic of the object to be observed;

(b) choosing a class of reference objects including n phantoms exhibiting n known values of the same physical magnitude;

(c) selecting j values $V_m$ of the supply voltage for the X-ray tube (11) at which calibration is to be performed;

(d) selecting a value of the product IS of the anode current I drawn by the X-ray tube during the exposure time S for each phantom associated with each value of the supply voltage $V_m$;

(e) installing a phantom in the path of the X-rays, adjusting the tube voltage to a value $V_m$, and integrating the radiation (16) that passes through the phantom as detected by the detector cell between the beginning of measurement and the instant at which the product IS is equal to the value selected in step (d), thereby obtaining a measurement M;

(f) calculating the efficiency D as given by the ratio M/IS;

(g) reiterating operations (e) and (f) for the same phantom for each of the (j−1) other selected values of the supply voltage $V_m$;

(h) reiterating steps (e), (f) and (g) for the (n−1) other phantoms;

(i) using a conventional estimation method, determining the analytic model $D = f(V_m, A)$ relating the values of efficiency D to the values of the physical magnitude A and of the supply voltage $V_m$; and (j) determining the inverse function of $f(V_m, A)$ written $g(V_m, D)$, thereby enabling A to be determined with known values of $V_m$ and D.

2. A method of measuring the equivalent thickness $E_p$ of an object with a radiological system calibrated by the method of claim 1 comprising the steps of placing the object in the path of the X-rays, adjusting the supply voltage $V_m$ of the X-ray tube, measuring the efficiency D, and calculating the equivalent thickness $E_p$ using the equation $E_p = g(V_m, D)$.

3. A method according to claim 1 for a radiological system having a plurality of configuration parameters and including the step of (k) reiterating operations (e) through (j) for each value of the configuration parameters.

4. A method according to claim 2, wherein it further includes the operation of displaying the calculated equivalent thickness $E_p$.

5. A calibration method according to claim 3 wherein the calibration parameters are grouped into classes and including performing the steps (e) through (j) for each reference configuration in each class (C), and further including determining for each element of the class (C) a weighting coefficient relative to the reference configuration by measuring the efficiency D at a supply voltage $V_m$ and for a given value of the physical magnitude A, and by defining the weighting coefficient of the configuration as the ratio between said measured efficiency D and the efficiency measured under analogous conditions using the reference configuration.

6. A calibration method according to claim 5, wherein the weighting coefficient is obtained by calculating the mean of the efficiency ratios as measured several different times for the same element of the class (C) under the same radiological conditions.

7. A calibration method according to claim 5, wherein the weighting coefficient is obtained by calculating the mean of the efficiency ratios as measured on one or more occasions for the same element of the class (C) with various different phantoms and for various different values of the supply voltage $V_m$.

8. A calibration method according to claim 7, wherein the physical magnitude A is the thickness $E_p$ of the phantom in the propagation direction of the X-rays.

9. A calibration method according to claim 1 wherein the physical magnitude A is the thickness $E_p$ of the phantom in the propagation direction of the X-rays.

10. A calibration method according to claim 9, wherein the analytic model is written in the form:

$$f(V_m, E_p) = \exp[f_1(V_m) + E_p \times f_2(V_m)]$$

where $f_1(V_m)$ and $f_2(V_m)$ are second order polynomials as follows:

$$f_1(V_m) = A_0 + A_1 V_m + A_2 V_m^2$$

$$f_2(V_m) = B_0 + B_1 V_m + B_2 V_m^2$$

11. A calibration method according to claim 10 wherein the inverse function $f(V_m, D)$ relating the measurement D and the supply voltage $V_m$ to the thickness $E_p$ is given by the equation:

$$g(V_m,D) = E_p = \frac{Ln(D) - f_1(V_m)}{f_2(V_m)}.$$

12. A method of measuring the equivalent thickness $E_p$ of an object by means of a radiological system calibrated using the method of claim 11, comprising the following steps:
(1) placing the object on the path of the X-rays;
(2) adjusting the supply voltage $V_m$ of the X-ray tube;
(3) measuring the efficiency D; and
(4) calculating the equivalent thickness $E_p$ using the equation $E_p = g(V_m, D)$.

13. A method of calibrating a radiological system for examining an object (13) wherein the system is of the type including an X-ray tube (11) having a supply voltage V adjustable to various different values $V_m$ either continuously or discretely, the tube emitting a beam of X-rays in the form of bursts of variable duration S, and having an anode current I, and a detector cell for detecting X-rays that have passed through the object to be examined and for converting a physical magnitude characteristic of the beam of X-rays into a measurement signal M such as an electrical signal, the method comprising the steps of:
(a) selecting a physical magnitude A which is characteristic of the object to be observed;
(b) choosing a class of reference objects including n phantoms exhibiting n known values of the same physical magnitude;
(c) selecting j values $V_m$ of the supply voltage for the X-ray tube (11) at which calibration is to be performed;
(d) selecting an exposure time S for each phantom associated with each value of the supply voltage $V_m$;
(e) placing a phantom in the path of the X-rays, adjusting the tube voltage to a value $V_m$, measuring the product IS of the anode current and exposure time and integrating the radiation (16) that passes through the phantom as detected by the detector cell during the selected exposure time S, thereby obtaining a measurement M;
(f) calculating the efficiency D as given by the ratio M/IS;
(g) reiterating operations (e) and (f) for the same phantom for each of the (j–1) other selected values of the supply voltage $V_m$;
(h) reiterating steps (e), (f) and (g) for the (n–1) other phantoms;
(i) using a conventional estimation method, determining the analytic model $D = f(V_m, A)$ relating the values of efficiency D to the values of the physical magnitude A and of the supply voltage $V_m$; and
(j) determining the inverse function of $f(V_m, A)$ written $g(V_m, D)$, thereby enabling A to be determined with known values of $V_m$ and D.

14. A calibration method according to claim 13 wherein the physical magnitude A is the thickness $E_p$ of the phantom in the propagation direction of the X-rays.

15. A calibration method according to claim 14 wherein the analytical model is written in the form $$f(V_m, E_p) = \exp[f_1(V_m) = E_p(f_2(V_m))]$$

where $f_1(V_m)$ and $f_2(V_m)$ are second order polynomials as follows:

$$f_1(V_m) = A_0 + A_1 V_m + A_2 V_m^2$$

$$f_2(V_m) = B_0 + B_1 V_m + B_2 V_m^2.$$

16. A method according to claim 13 for a radiological system having a plurality of configuration parameters and including the step of
(k) reiterating operations (e) through (j) for each value of the configuration parameters.

17. A calibration method according to claim 16 wherein the calibration parameters are grouped into classes and including performing the steps (e) through (j) for each reference configuration in each class (C), and further including
determining for each element of the class (C) a weighting coefficient relative to the reference configuration by measuring the efficiency D at a supply voltage $V_m$ and for a given value of the physical magnitude A, and by defining the weighting coefficient of the configuration as the ratio between said measured efficiency D and the efficiency measured under analogous conditions using the reference configuration.

18. A calibration method according to claim 17 and including obtaining the weighting coefficient by calculating the mean of the efficiency ratios measured a plurality of times for the same element of the class (C) under the same radiological conditions.

19. A calibration method according to claim 17 and including obtaining the weighting coefficient by calculating the mean of the efficiency ratios measured one or more times for the same element of the class (C) with different phantoms each time and for different values of the supply voltage $V_m$ each time.

20. A calibration method according to claim 19 wherein the physical magnitude A is the thickness $E_p$ of the phantom in the propagation direction of the X-rays.

21. A calibration method according to claim 15 wherein the inverse function $f(V_m, D)$ relating the measurement D and the supply voltage $V_m$ to the thickness $E_p$ is given by the equation $$g(V_m,D) = E_p = \frac{Ln(D) - f_1(V_m)}{f_2(V_m)}.$$

22. A method of measuring the equivalent thickness $E_p$ of an object with a radiological system calibrated using the method of claim 21 and comprising the steps of
placing the object in the path of the X-rays,
adjusting the supply voltage $V_m$ of the X-ray tube,
measuring the efficiency D, and
calculating the equivalent thickness $E_p$ using the equation $E_p = g(V_m, D)$.

23. A method of measuring the equivalent thickness $E_p$ of an object with a radiological system calibrated using the method of claim 13 and comprising the steps of
placing the object in the path of the X-rays,
adjusting the supply voltage $V_m$ of the X-ray tube,
measuring the efficiency D, and
calculating the equivalent thickness $E_p$ using the equation $E_p = g(V_m, D)$.

24. A method according to claim 23 and further including the step of displaying the calculated equivalent thickness $E_p$.

25. A method of calibrating a radiological system for examining an object (13) wherein the system is of the type including an X-ray tube (11) having a supply voltage V adjustable to various different values $V_m$ either continuously or discretely, the tube emitting a beam of X-rays in the form of bursts of variable duration S, and having an anode current I, and a detector cell for detecting X-rays that have passed through the object to be examined and for converting a physical magnitude characteristic of the beam of X-rays into a measurement signal M such as an electrical signal, the method comprising the steps of:

(a) selecting a physical magnitude A which is characteristic of the object to be observed;

(b) choosing a class of reference objects including n phantoms exhibiting n known values of the same physical magnitude;

(c) selecting j values $V_m$ of the supply voltage for the X-ray tube (11) at which calibration is to be performed;

(d) selecting an exposure time S for each phantom associated with each value of the supply voltage $V_m$;

(e) placing a phantom in the path of the X-rays, adjusting the tube voltage to a value $V_m$, measuring the product IS of the anode current and exposure time and integrating the radiation (16) that passes through the phantom as detected by the detector cell during the selected exposure time S, thereby obtaining a measurement M;

(f) calculating the efficiency D as given by the ratio M/IS;

(g) reiterating operations (e) and (f) for the same phantom for each of the (j−1) other selected values of the supply voltage $V_m$;

(l) reiterating steps (e) and (f) for each of the (n−1) other phantoms at a selected value of the supply voltage $V_m$;

(m) determining a first analytic model $G_A(V_m)$ relating the efficiency value D to the supply voltage $V_m$ for a fixed value A;

(n) determining a second analytical model $H_{V_m}(A)$ relating the efficiency values D to the values of the physical magnitude A for fixed $V_m$; and (o) Determining an analytical model $D=f(V_m, A)$, resulting from multiplying the functions $G_A(V_m)$ and $H_{V_m}(A)$, thereby reducing the number of measurements required for calibration purposes.

26. A method of measuring the equivalent thickness $E_p$ of an object with a radiological system calibrated using the method of claim 25 and comprising the steps of placing the object in the path of the X-rays, adjusting the supply voltage $V_m$ of the X-ray tube, measuring the efficiency D, and calculating the equivalent thickness $E_p$ using the equation $E_p = g(V_m, D)$.

27. A method according to claim 26 and further including the step of displaying the calculated equivalent thickness $E_p$.

28. A calibration method according to claim 25 wherein the calibration parameters are grouped into classes and including performing the steps (e) through (j) for each reference configuration in each class (C), and further including determining for each element of the class (C) a weighting coefficient relative to the reference configuration by measuring the efficiency D at a supply voltage $V_m$ and for a given value of the physical magnitude A, and by defining the weighting coefficient of the configuration as the ratio between said measured efficiency D and the efficiency measured under analogous conditions using the reference configuration.

29. A calibration method according to claim 28 and including obtaining the weighting coefficient by calculating the mean of the efficiency ratios measured a plurality of times for the same element of the class (C) under the same radiological conditions.

30. A calibration method according to claim 28 and including obtaining the weighting coefficient by calculating the mean of the efficiency ratios measured one or more times for the same element of the class (C) with different phantoms each time and for different values of the supply voltage $V_m$ each time.

31. A calibration method according to claim 30 wherein the physical magnitude A is the thickness $E_p$ of the phantom in the propagation direction of the X-rays.

32. A calibration method according to claim 25 wherein the physical magnitude A is the thickness $E_p$ of the phantom in the propagation direction of the X-rays.

33. A calibration method according to claim 32 wherein the analytical model is written in the form $$f(V_m, E_p) = \exp[f_1(V_m) = E_p(f_2(V_m))]$$

where $f_1(V_m)$ and $f_2(V_m)$ are second order polynomials as follows:

$$f_1(V_m) = A_0 + A_1 V_m + A_2 V_m^2$$

$$f_2(V_m) = B_0 + B_1 V_m + B_2 V_m^2.$$

34. A calibration method according to claim 33 wherein the inverse function $f(V_m, D)$ relating the measurement D and the supply voltage $V_m$ to the thickness $E_p$ is given by the equation $$g(V_m, D) = E_p = \frac{Ln(D) - f_1(V_m)}{f_2(V_m)}.$$

35. A method of measuring the equivalent thickness $E_p$ of an object with a radiological system calibrated using the method of claim 34 and comprising the steps of placing the object in the path of the X-rays, adjusting the supply voltage $V_m$ of the X-ray tube, measuring the efficiency D, and calculating the equivalent thickness $E_p$ using the equation $E_p = g(V_m, D)$.

* * * * *